United States Patent [19]
Martin

[11] Patent Number: 5,921,964
[45] Date of Patent: Jul. 13, 1999

[54] SAFETY BLOOD COLLECTING DEVICE

[76] Inventor: Robin Martin, Rte. 5, Box 3766, Lufkin, Tex. 75901

[21] Appl. No.: 08/014,682

[22] Filed: Feb. 8, 1993

[51] Int. Cl.[6] .................................................... A61M 5/32
[52] U.S. Cl. ........................................... 604/198; 600/578
[58] Field of Search .................................... 604/198, 199, 604/110, 192, 263, 197, 195, 162, 167, 187, 196; 128/764, 765, 763, 919

[56] References Cited

U.S. PATENT DOCUMENTS

| | | | |
|---|---|---|---|
| 5,137,521 | 8/1992 | Wilkins | 604/198 |
| 5,201,708 | 4/1993 | Martin | 604/110 |
| 5,217,025 | 6/1993 | Okamura | 128/765 |
| 5,269,761 | 12/1993 | Stehrenberger et al. | 604/110 |
| 5,279,566 | 1/1994 | Kline, Jr. et al. | 604/110 |

FOREIGN PATENT DOCUMENTS

| | | | |
|---|---|---|---|
| 8904141 | 5/1989 | WIPO | 128/763 |

*Primary Examiner*—Ronald Stright
*Assistant Examiner*—A. T. Nguyen
*Attorney, Agent, or Firm*—Keaty & Keaty

[57] ABSTRACT

The invention relates to a safety blood collecting device adapted to prevent accidental puncturing of attending medical personnel by an infected blood collecting needle. The blood collecting device has a forward conical portion which is provided with a vein aligning groove to allow convenient positioning of the needle guard in relation to the vein of the patient for precise injection of the needle. One or more resilient depressible locking tabs are carried by the needle guard and extend through corresponding aligned openings formed in the casing to lock the needle guard in an extended position covering the needle. When the locking tabs are depressed and an inward pressure is exerted on the forward end of the needle guard, the needle guard can be moved against the tension of a coil spring inside the casing and uncover the blood collecting needle to allow withdrawing of the blood from the patient.

19 Claims, 3 Drawing Sheets

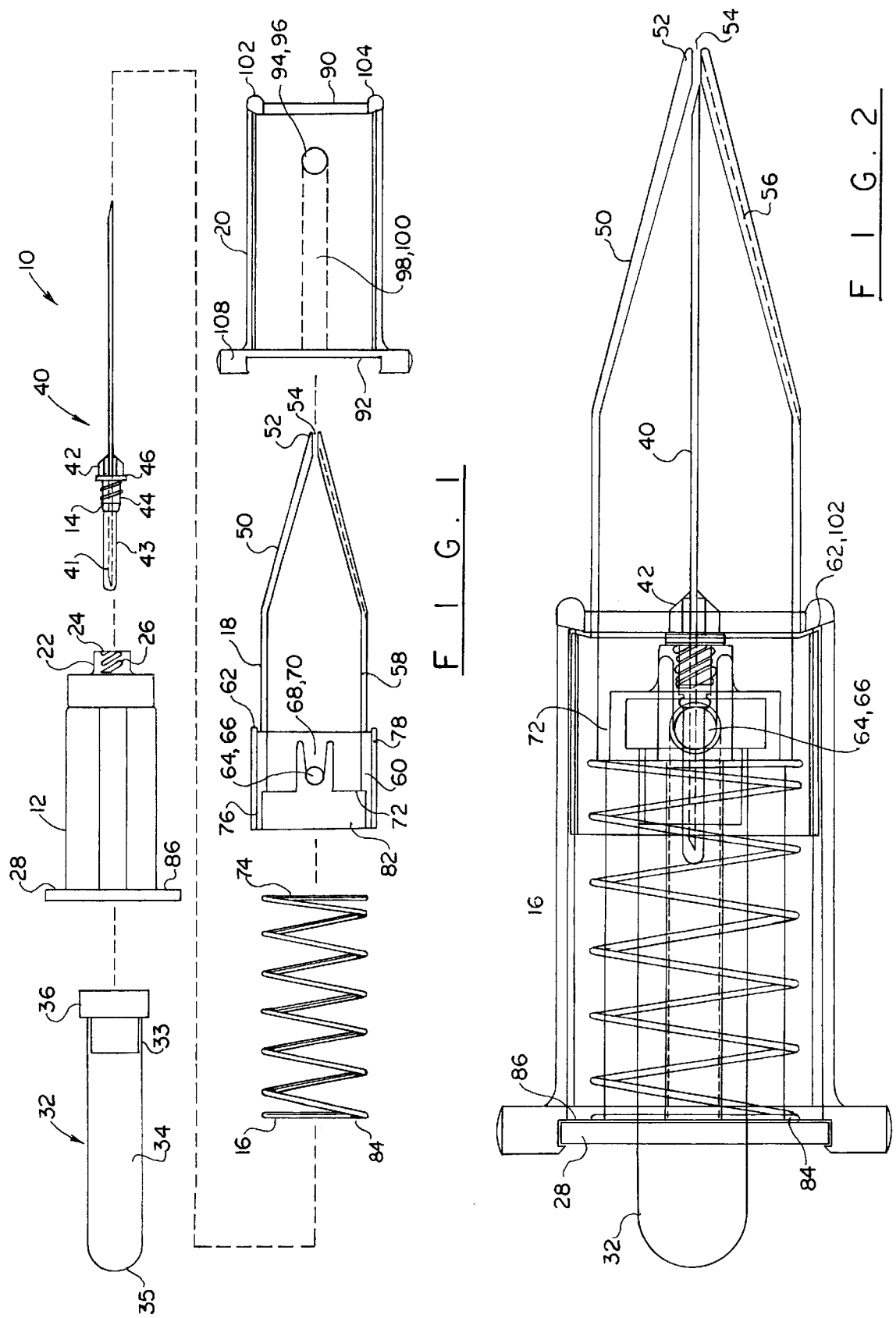

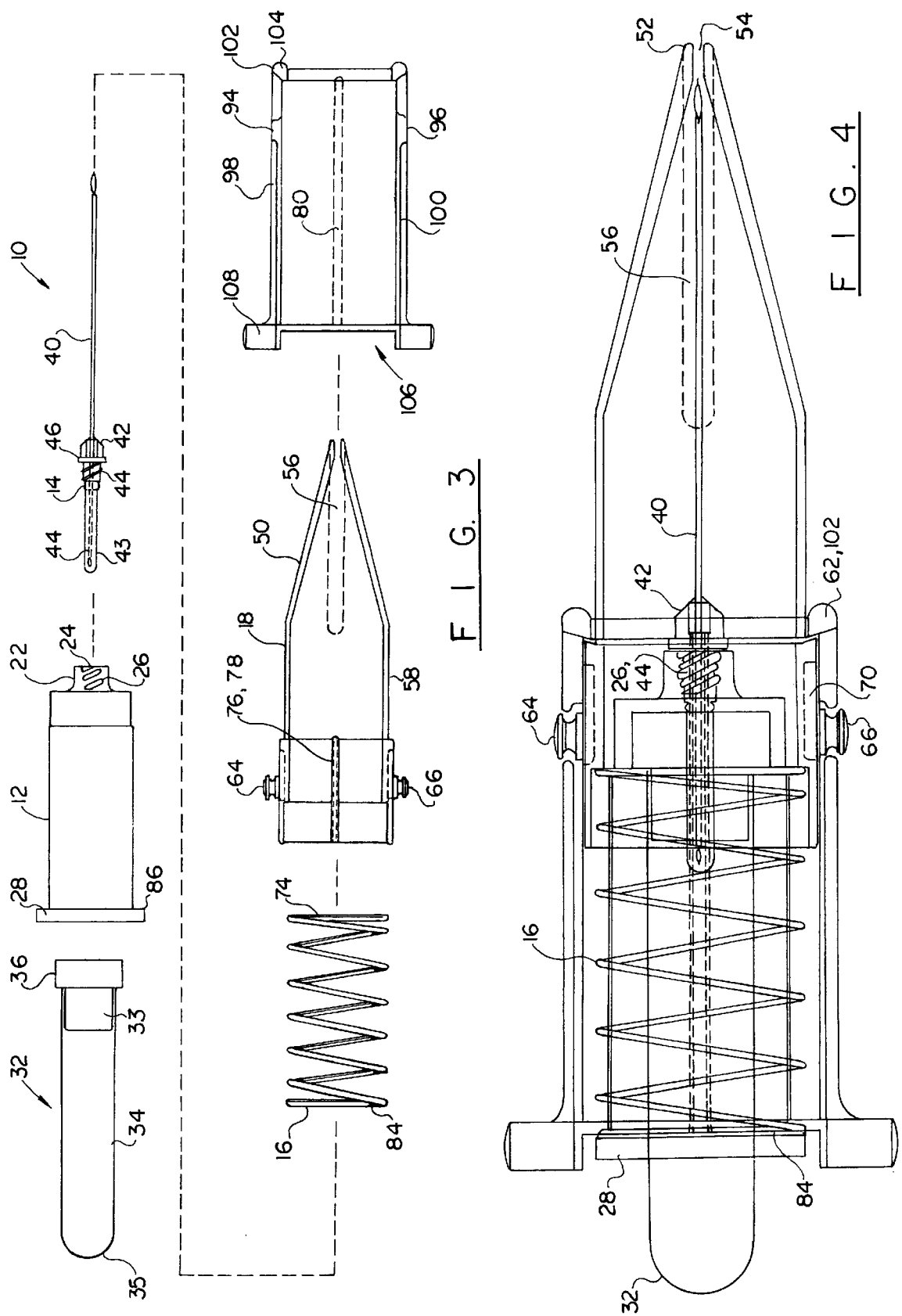

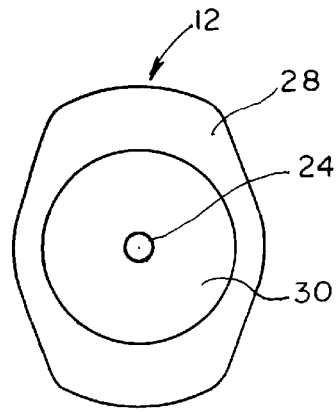
F I G. 5
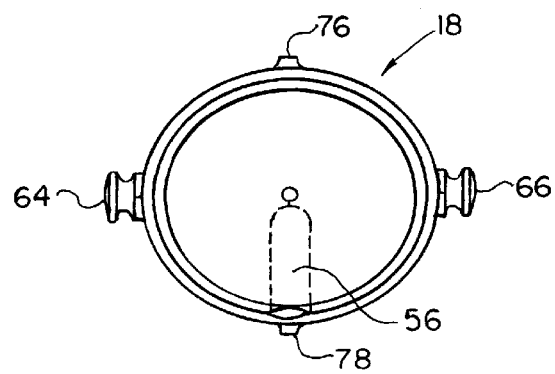
F I G. 6
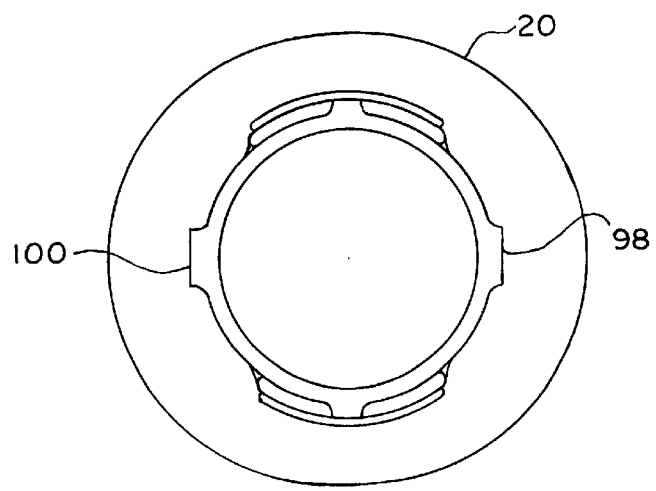
F I G. 7

SAFETY BLOOD COLLECTING DEVICE

BACKGROUND OF THE INVENTION

This invention relates to medical equipment, and more particularly to a safety blood Collecting device designed to prevent accidental needle stick injuries by medical personnel, for example during drawing of a blood specimen of a patient.

The ever increasing spread of diseases transmitted by blood and other bodily fluids, such as Acquired Immune Deficiency Syndrome and Hepatitis B creates a real threat to medical personnel of accidental, inadvertent puncturing of the skin by a blood collecting needle which has been in contact with an infected patient and of the transmittal of the often fatal disease to the unfortunate medical attendant. Despite educational programs carried by many hospitals, accidents continue to happen with an unfortunate effect of medical personnel being infected through coming in contact with bodily fluids of a patient.

Various attempts have been made to resolve this problem by proposing to use a protective needle guard, which would cover the needle when the blood collecting device is not in use and prevent the needle from being exposed during those times. However, such devices are expensive to manufacture and difficult to use, requiring several steps in preparation of the blood collecting device for utilization and, so far, have not found wide acceptance in the medical profession.

The present invention contemplates elimination of drawbacks associated with prior art and provision of an improved safety blood collecting device particularly adapted for drawing blood from a patient and which is easy to use and inexpensive to manufacture.

SUMMARY OF THE INVENTION

It is, therefore, a general object of the present invention to provide a self-locking safety blood collecting device which is designed to prevent premature exposure of the needle.

It is another object of the present invention to provide a locking device for covering the needle at all times before insertion of the needle into the vein.

It is a further object of the present invention to provide a needle guard which is particularly adapted for aligning the needle about the vein of a patient.

These and other objects are achieved through a provision of a safety blood collecting device which comprises a tubular needle holder carrying a needle assembly on one end thereof and which is surrounded by a tension spring which abuts an enlarged flange on the free end of the holder. A needle guard is mounted in a partially surrounding relationship over the needle holder and covers the needle assembly in its entirety when the blood collecting device is not in use. The needle guard has a forward most conical portion which is provided with a narrow opening in its apex.

The needle, when in use, is allowed to pass through the opening and enter the body of the patient. The conical portion is further provided with a vein alignment groove formed in the conical wall and extending through substantially entire length thereof. When in use, the groove is aligned over the vein of the patient, thus ensuring proper alignment of the needle during drawing of the blood.

A cylindrical middle portion of the needle guard carries a pair of resiliently depressible locking tabs which snap out of corresponding openings formed in the casing when the blood collecting device is not use. The casing surrounds the middle portion of the needle guard and the needle holder to which the casing is fixedly attached. The inner grooves formed in the casing allow sliding of the depressed locking tabs therein. A tension spring continuously urges the needle guard in covering relationship over the needle assembly, but the force of the tension spring is overcome once a pushing pressure is applied to the tip of the needle guard. To prevent puncturing of the skin of the patient by the needle guard, the tip of the conical portion is made with rounded walls.

A pair of alignment runners are formed on the middle portion of the needle guard, said runners being slidably received within grooves formed in the inner wall of the casing at a 90 degree angle in relation to the locking tab grooves.

A blood collecting reservoir is removably positioned within a -needle holder in co-alignment with the needle assembly, so as to allow collection of the blood sample from a patient and detachment of the reservoir once the necessary amount has been collected.

BRIEF DESCRIPTION OF THE DRAWINGS

Reference will now be made to the drawings, wherein like parts are designated by like numerals and wherein:

FIG. 1 is an exploded view of the device in accordance with the present invention.

FIG. 2 is a view of the device in an assembled state.

FIG. 3 is an exploded view of the device in accordance with the present invention looking at a 90 degree angle from the view of FIG. 1.

FIG. 4 is an assembled view of the device taken at a 90 degree angle from FIG. 2.

FIG. 5 is an end view of the needle holder.

FIG. 6 is an end view of the needle guard; and

FIG. 7 is an end view of the casing.

DETAILED DESCRIPTION OF THE PREFERRED EMBODIMENT

Referring now to the drawings in more detail, numeral 10 designates the device in accordance with the present invention. The safety blood collecting device comprises a needle holder 12, a needle assembly 14, a compression tension spring 16, a needle guard 18 and a casing 20. The needle holder 12 is a hollow, generally cylindrical body having a reduced diameter nose portion 22 provided with a central opening 24 therein, and internal threads schematically shown and designated by numeral 26. The holder 12 is provided with an enlarged diameter end plate 28 which encircles the central opening 30 made in the holder 12. As can be seen in FIG. 5, the opening 24 is considerably smaller in diameter than the opening 30 which defines the interior chamber formed in the holder 12.

Detachably mounted within the holder 12 is a blood collecting reservoir 32 which is similar to conventional blood collecting tubes in that a vacuum is created in the chamber 34, and the reservoir is sealed by a plug 36 covering the open end 33 of the reservoir. The opposite end 35 is made closed, as can be seen in FIG. 1. The plug 36 is made from a soft resilient material having plastic memory.

The needle assembly 14 has an elongated sharp-ended needle 40 and a securing portion 42 which comprises an externally threaded part 44 extending inwardly from a plate 46. When assembled with the holder 12, the plate 46 contacts the nose portion 22, while the threaded part 44 fits within the opening 24 and engages with the threads 26. The opposite, inner part 41 of the needle 40 is enclosed in a sheath 43 which can be made of rubber thin enough to be punctured by the needle part 41 without application of any substantial force. The sheath 43 passes through the opening 24 into the holder 12. When the reservoir 32 is engaged with the holder 12, immediately before collecting blood from a patient, the needle part 41 punctures the sheath 43, then plug 36 and forces its way into the tube 32 opening fluid communication between the sharp end of the needle 40 and the interior chamber 34 of the tube 32.

The needle guard 18 comprises a conical forward portion 50 which is provided with a narrow rounded wall apex 52 having a small diameter opening 54 in the center thereof. Formed in the conical wall is a vein stabilizing groove 56 which extends from the tip, or apex 52 inwardly towards the middle portion 58 of the needle guard 18. The groove 56 is an elongated narrow groove having a width approximating the width of a human vein. The function of the groove 56 will be explained in more detail hereinafter. Attached to the opposite end of the middle portion 58 is an inner part 60 which is greater in diameter than the portion 58 and which is provided with inwardly inclined shoulder 62 formed at the line of connection between the portions 58 and 60.

A pair of depressible locking tabs 64 and 66 are attached to diametrically opposite sides of the portion 60 and are carried by their supporting members 68 and 70, respectively. The supporting members 68 and 70 are flexible and yield when compression is applied to the locking tabs 64 and 66, allowing the tabs to move inwardly in relation to the casing 20, as will be described below, and push the tabs 64 and 66 outwardly through the specially designed openings in the casing, when the tabs are released.

Formed a distance from the tabs 64 and 66 is an annular shoulder 72 which forms a first abutting shoulder for the end 74 of the compression spring 16.

Also formed on diametrically opposite sides of the portion 60 is a pair of elongated runners 76 and 78 which extend along the length of the portion 60 and are adapted for engagement with corresponding runner grooves 80 formed in the body of the casing 20. The runners 76 and 78 are narrow strips which are fixedly attached to the exterior surface of the portion 60 at 90 degrees from the locking tabs 64 and 66. The runners 76 and 78 facilitate alignment of the needle guard 18 in its sliding movement within the casing 20.

A circular cutout groove 82 formed in the proximate end of the needle guard 18 has a diameter slightly greater than the diameter of the compression spring 16, so that a portion of the spring 16 fits within the cutout 82, as can be better seen in FIGS. 2 and 4. The opposite end 84 of the spring 16 abuts against the inner surface 86 of the needle holder 12, when the blood collecting device is assembled.

The casing 20 comprises an elongated cylindrical hollow body with a first open end 90 and a second open end 92. Formed in diametrically opposite locations in the walls of the casing 20 are a pair of openings 94 and 96 which are sized to allow the locking tabs 64 and 66, respectively, to extend outwardly therethrough. The openings 94 and 96 communicate with the respective locking tab grooves 98 and 100 which allow movement of the locking tabs 64 and 66 therein when the needle guard 18 moves telescopically inside the casing 20.

An annular, inwardly inclined shoulder 102 is formed at a distal end of the casing 20, the shoulder 102 being inclined at an angle which matches the angle of the shoulder 62 formed on the needle guard 18, so that when the shoulders 62 and 102 come into contact, their angles match. The end 90 of the casing 20 has a rounded wall 104, while the end 92 is formed with an annular recess 106. An enlarged diameter flange 108 surrounds the recess 106 in a circumferential relationship. The end plate 28 of the needle holder 12 fits within the recessed groove 106 and is fixedly attached to casing 20 within said recessed grove 106, as can be better seen in FIGS. 2 and 4, closing the open end 92.

When assembled, the holder 12 is engaged with the needle assembly 14 and is positioned within the needle guard 18 in such a manner that the needle 40 extends in the hollow interior of the needle guard 18. Since the overall length of the needle guard 18 is greater than the length of the needle 40, no portion of the needle extends outwardly from the opening 54 in the Lip 52 when the blood collecting device is not in use. The spring 16 is compressed between the flange 28 and the shoulder 72 and extends in a surrounding relationship about the needle holder 12. The casing 20 is slid over the needle guard 18 until the locking tabs 64 and 66 are forced through the openings 94 and 96, respectively.

Once assembled, the needle guard 18 is prevented from telescopical movement in relation to the casing 20 by the outwardly extending locking tabs 64 and 66. However, when the locking tabs 64 and 66 are compressed, they move into the grooves 98 and 100 and the guard 18 can telescopically move into the casing 20 when a push force is applied to the tip 52. The guard 20 moves against the expanding force of the spring 16, allowing the tip of the needle 40 to be injected for performing an injection.

Prior to injection, the user can conveniently align the conical portion 50 above the vein of the patient in such a manner that the groove 56 is substantially oriented in the direction of the vein and surrounds it on the skin of the patient, assisting the user to keep the needle 40 in alignment with the vein. When the needle guard 18 is moved as described above, the tip of the needle 40 can be inserted into the vein of the patient and the blood can be drawn by forcing the vacuum tube 32 over the opposite end of the double sided blood collecting needle 40 inside the needle holder 12. As the vacuum tube is advanced within the needle holder, the second end of the blood collecting needle punctures the vacuum tube plug and the vacuum inside the vacuum tube aspirates the blood from the patient. Since the plug 36 is made of soft material the punctured area will automatically seal around the needle 41. The sheath at this time is folded and pushed forward by the plug 36. Once the operation is complete, the user withdraws the device and the expansion force of the spring 16 will force the cone 50 outwardly from the casing 20, again concealing the needle 40 and forcing the locking tabs 64 and 66 to extend through the openings 94 and 96, respectively. The user then disengages the tube 32 from the holder 12. The plastic memory of the plug 36 will seal the punctured opening retaining the blood in the tube 32.

The device 10 of the present invention can be manufactured from any convenient material, such as plastic, with the exception of the needle 40 which should be preferably made of metal. It is envisioned that various sized blood collecting devices can be manufactured utilizing the basic concept of the instant invention giving the user a choice of various volume holders 12, as well as different size needles 40.

Many changes and modifications can be made within the design of the present invention without departing from the spirit thereof. I, therefore, pray that my rights to the present invention be limited only by the scope of the appended claims.

I claim:

1. A self-locking safety blood collecting device, comprising:
   an elongated tubular casing;
   a needle holder having a needle assembly, which comprises a needle with a pointed needle tip, affixed thereto, said needle holder being securely attached to one end of the casing;
   an elongated hollow needle guard telescopically coaxially engaged with the casing, said needle guard being movable between an extended position, substantially covering the needle assembly and selectively variable, retracted positions allowing injection of the tip of the needle, said needle guard being provided with an elongated alignment groove extending a distance inwardly from a forwardmost end of the needle guard to allow alignment of the needle guard in relation to a vein of a patient.

2. The device of claim 1, further comprising a tension spring means continuously urging the needle guard to the extended position, thereby preventing accidental movement of the needle guard into the retracted positions even after the locking means have been depressed.

3. The device of claim 1, wherein said needle holder comprises an elongated cylindrical body having a reduced diameter nose portion provided with internal threads, and said needle assembly being provided with an externally threaded part which threadably engages with the nose portion of the needle holder.

4. The device of claim 3, wherein said needle holder is provided with an enlarged diameter flange fixedly attached to the needle holder at an end opposite the nose portion said flange forming a shoulder against which one end of the tension spring means abuts.

5. The device of claim 4, wherein an annular outwardly open recess is formed in one end of the casing, said recess being sized and shaped to receive the flange of the needle holder therein.

6. The device of claim 4, wherein said needle holder is sized and shaped to detachably receive a blood collecting reservoir in at least partially enclosing relationship.

7. The device of claim 6, wherein said needle assembly is provided with an elongated needle, an inner part of the needle being enclosed in a sheath, said sheath being fixedly attached to the threaded part of the needle assembly.

8. The device of claim 7, wherein said inner part is sharpened so as to allow penetration of the inner needle part into the blood collecting reservoir immediately before collecting a blood sample from a patient.

9. The device of claim 1, wherein said needle guard comprises a forward conical portion having an opening in its apex through which the needle tip extends during use.

10. The device of claim 9, wherein the alignment groove extends from the apex of the conical portion substantially through entire length of the conical portion.

11. The device of claim 9, wherein said needle guard is provided with a substantially cylindrical middle portion which carries at least one resilient depressible locking means for locking the needle guard in the extended position.

12. The device of claim 9, wherein an annular shoulder is formed in the needle guard a distance from said locking means, said shoulder forming an abutting surface for one end of a tension spring, which continuously urges the needle guard outwardly into the extended position, said tension spring being mounted in circumferential relationship about said needle holder.

13. The device of claim 9, wherein an edge of a forwardmost end of the needle guard is rounded to prevent accidental puncturing of the skin of the patient during use.

14. The device of claim 1, further comprising a resilient depressible means for locking the needle guard in the extended position, said needle guard locking means being carried by the needle guard a distance away from the forwardmost end of the needle guard.

15. The device of claim 14, wherein said casing is provided with at least one opening through which the resilient depressible locking means extend.

16. The device of claim 15, wherein one or more elongated grooves are formed in an inner wall of the casing to allow sliding of the resilient depressible locking means therein.

17. A self-locking safety blood collecting device, comprising:
   an elongated tubular casing defined by an annular wall, said wall having at least one opening therethrough, at least one elongated groove formed in an inner surface of the annular wall in communication with the opening, said casing being provided with an annular outwardly open recess formed in one end thereof;
   a needle holder having a needle assembly affixed thereto, said needle holder having an enlarged diameter flange which securely engages the casing by fitting within the open recess of the casing, said needle holder carrying a needle assembly at one of its ends and an enlarged diameter flange on its opposite end;
   an elongated hollow needle guard telescopically coaxially engaged within the casing, said needle guard being movable between an extended position, substantially covering the needle assembly and selectively variable, retracted positions exposing the tip of the needle, said needle guard being provided with an elongated groove extending a distance inwardly from the forwardmost tip of the needle guard to allow alignment of the needle guard in relation to a vein of a patient, said needle guard having a first conical portion, wherein the elongated groove is located, and a second cylindrical portion which carries at least one locking tab which is mounted on a resilient depressible support allowing movement of said at least one locking tab towards an axis of the needle guard and away therefrom, said at least one locking tab extending through at least one opening in the casing when the blood collecting device is not in use;
   a tension spring means mounted in circumferential relationship about the needle holder which is mounted within the casing, said spring having a first end which urges against the enlarged diameter flange of the needle holder and which urges against said needle guard at its opposite end, thereby continuously forcing the needle guard into the extended position.

18. The device of claim 17, wherein said alignment groove extends a distance inwardly from a forwardmost tip of the conical portion of the needle guard towards the second portion of the needle guard.

19. The device of claim 18, wherein said needle holder threadably engages with a needle assembly, and wherein said needle guard has a length which is at least slightly greater than the length of the needle assembly, so as to prevent exposure of the needle tip outwardly from the needle guard when the blood collecting device is not in use.

* * * * *